United States Patent [19]

McIntosh

[11] Patent Number: 5,399,774
[45] Date of Patent: Mar. 21, 1995

[54] PROCESS FOR THE PRODUCTION OF KETENE DIMERS

[75] Inventor: Paul S. McIntosh, Bristol, England

[73] Assignee: Eka Nobel AB, Bohus, Sweden

[21] Appl. No.: 198,263

[22] Filed: Feb. 18, 1994

[30] Foreign Application Priority Data

Feb. 22, 1993 [SE] Sweden .................................. 9300583

[51] Int. Cl.$^6$ ............................................. C07C 45/45
[52] U.S. Cl. ...................... 568/301; 568/302
[58] Field of Search .............................. 568/301, 302

[56] References Cited

FOREIGN PATENT DOCUMENTS

| | | |
|---|---|---|
| 0550107 | 7/1993 | European Pat. Off. . |
| 550107 | 7/1993 | European Pat. Off. ............ 568/301 |
| 748980 | 12/1944 | Germany . |
| 2327988 | 1/1975 | Germany . |
| 2335488 | 2/1975 | Germany . |
| 3434212 | 3/1986 | Germany . |
| 63-264544 | 11/1988 | Japan . |
| 101789 | 12/1991 | Romania . |

OTHER PUBLICATIONS

Abstract of JP 63-264544, Kokai, Nov. 1, 1988.

*Primary Examiner*—Johann Richter
*Assistant Examiner*—Michael B. Hydorn
*Attorney, Agent, or Firm*—Burns, Doane, Swecker & Mathis

[57] ABSTRACT

Production of ketene dimers from fatty acid halides by reaction with tertiary amines whereby the tertiary amine is used both as a reactant and as a solvent/diluent. In the process at least 1.15 moles of tertiary amine is used per mole of fatty acid halide and the process is carried out in the substantial absence of an additional solvent, whereby the produced ketene dimer is obtained by stripping of the tertiary amine followed by separation of formed crystals of tertiary amine hydrogen halide by acid extraction.

14 Claims, No Drawings

PROCESS FOR THE PRODUCTION OF KETENE DIMERS

The present invention relates to a process for the production of ketene dimers from fatty acid halides and tertiary amines and more particularly to a process for the production of ketene dimers in which the tertiary amine is used both as a reactant and as solvent/diluent and the process is carried out in the substantial absence of an additional solvent, whereby the produced ketene dimer is obtained by stripping of the tertiary amine followed by separation of formed crystals of tertiary amine hydrogen halide by acid extraction.

Long-chain "alkyl" ketene dimers (AKD) are extensively used in the papermaking industry as sizing agents and usually in the form of aqueous dispersions comprising cationic starch or cationic synthetic polymers as dispersing agents. Long-chain alkyl ketene dimers are produced by removal of hydrogen halide from fatty acid halides. The intermediate ketene is highly reactive and dimerizes. Conventionally the production of long-chain alkyl ketene dimers is carried out by addition of a tertiary amine to a fatty acid chloride substrate in an organic solvent, or by addition of fatty acid chloride to a tertiary amine in an organic solvent. The tertiary amine is usually used in a small molar excess, e.g. 1.1 moles of tertiary amine per mole of fatty acid chloride. The tertiary amine removes hydrogen chloride from the fatty acid chloride and crystals of amine hydrochlorides are formed. These crystals and the small excess of amine are then removed from the reaction mixture. This is usually made by acid extraction, thereby the remaining tertiary amine is converted to an amine salt soluble in the acid extraction medium. The produced AKD is obtained by evaporation of the solvent from the organic extraction phase. In commercial processes the acid extraction medium is usually worked-up by neutralisation with alkali to liberate free amine from the amine salt and finally the tertiary amine is dehydrated for re-use in the process.

The organic solvents which are used are inert with regard to the starting materials and the end-product. As inert solvents alkanes, cycloalkanes or aromatic hydrocarbons can be used. Usually aromatic hydrocarbons, such as toluene and 1,2-dichloropropane, are used in commercial processes. The amount of solvent is usually fairly high and most often at least 0.8 parts solvent as to 1 part fatty acid chloride is used. The solvent acts both as a solvent for the fatty acid halide and the AKD and as a diluent to keep the formed crystals apart during the reaction and thereby to prevent growth of the crystals resulting in inclusion of the starting materials and end-products. Such crystal growth with inclusions leads to decreased yield. All work with organic solvents, such as toluene, is of course undesirable from an environmental point of view and requires stringent safety measures. Furthermore, it is extremely difficult to remove all solvent from the produced AKD and this will thus usually contain about 0.1 to 0.6 per cent by weight of solvent, which of course is undesirable and which causes problems at the use of the AKD as sizing agent. Thus the solvent will be present in the paper produced, effluent from the paper machine and in exhaust from dryers.

Attempts to reduce the amount of inert organic solvents in the production of ketene dimers have not been successful. This is to a great extent due to the crystal growth and the shape of the crystals formed. The dendritic growth of the crystals of tertiary amine hydrohalide results in "needle-shaped" crystals and/or crystals having dendritic side branches, leading to an undesirably high viscosity in the reaction mixture. Thus it becomes very difficult to stir the reactor contents and heat transfer problems arises. In addition, the crystal growth occuring in the presence of only a small amount of inert organic solvent usually leads to inclusions and substantially decreased yield.

The present invention aims at providing a process for the production of ketene dimers from fatty acid halides and tertiary amines where the tertiary amine is used both as a reactant and solvent/diluent and the process is carried out in the substantial absence of an additional solvent. The present invention thus relates to a process as further defined in the claims. More specifically, the present invention relates to a process for the production of ketene dimers from fatty acid halides and tertiary amines where at least 1.15 moles of tertiary amine is used per mole of fatty acid halide and the process is carried out in the substantial absence of an additional solvent, whereby the produced ketene dimer is obtained by stripping of the tertiary amine followed by separation of formed crystals of tertiary amine hydrogen halide by acid extraction.

According to the present invention it has been found that it is possible to produce ketene dimers from fatty acid halides utilizing a tertiary amine both as a reactant and solvent/diluent. Hereby the present process makes it possible to entirely dispense with additional solvents and to avoid all problems connected with solvents and still gives as good yields and as high purity of the product as the conventional solvent-based processes. In the present process the tertiary amine can be used in a large molar excess with regard to the fatty acid halide, i.e. a much higher than normal amount of tertiary amine can be used and, hence, the problems connected with the growth and shape of the crystals formed in the reaction can be avoided or at least minimized. In order to provide both a technically and economically operable process using an excess of tertiary amine it has been found that it is necessary to work-up the reaction mixture by stripping of the tertiary amine followed by acid extraction. In the absence of the stripping step it will be necessary to use an undesirably high amount of acid in the extraction step to separate the excess of tertiary amine and formed crystals from the organic ketene dimer phase, and the work-up of the aqueous extraction phase will require use of a very high amount of alkali in the neutralisation step to liberate free amine. Furthermore, the dehydration of the water-containing liberated tertiary amine will require an undesirably high amount of dehydrating agent or a much higher than normal amount of tertiary amine will have to be distilled before re-use in the process. The stripping step is further advantageous in that the recovered tertiary amine can be re-used directly in the process. Thus the stripping step according to the present process facilitates work-up of the reaction mixture and makes it possible to reduce the amount or volume of work-up chemicals. Accordingly, the use of an excess of tertiary amine in combination with stripping of the unreacted amine before the acid extraction step lead to a technically as well as economically advantageous process. Thus the present process makes it possible to increase productivity and to better utilize reaction equipment.

The present process is carried out in the substantial absence of additional solvents and hereby is meant that not more than 10% by weight, based on the amount of fatty acid halide, of materials which act as solvents/diluents and which are inert with regard to the starting materials and the end-product, such as toluene etc., are present during the process. If additional solvents are present in amounts higher than 10% the produced AKD will be disadvantageous in that it will contain too much solvent. Up to this limit the present process will, however, give productivity advantages in comparison with known solvent based processes. Suitably not more than 5% by weight, and preferably not more than 2% by weight, of additional solvent, based on the fatty acid halide, is used in the process. The greatest advantage of the present process is, of course, that it is possible to entirely avoid the use of additional solvents.

The starting material for the present process is a fatty acid halide, suitably with from 12 to 22 carbon atoms and preferably with from 16 to 18 carbon atoms, or a mixture of such fatty acid halides. The fatty acid halide can be a halide of a saturated or unsaturated fatty acid and as some examples can be mentioned halides of lauric acid, myristic acid, palmitic acid, stearic acid, arachidic acid, palmitoleic acid, oleic acid etc. Halides of naturally occurring fatty acids such as those from coco and tallow can of course also be used. The fatty acid halide is usually a chloride and stearic acid chloride is of particular technical interest.

The tertiary amine used in the present process can be a monoamine or diamine. Since the tertiary amine is used as a replacement for a solvent it must be liquid at the reaction conditions. The tertiary amine should be easy to evaporate to facilitate the stripping of the tertiary amine from the reaction mixture after completed reaction. The tertiary amine is suitably a monoamine of the formula $R_1R_2R_3N$, wherein $R_1$, $R_2$ and $R_3$ independent of each other can be alkyl, alkenyl or cycloalkyl groups having from 1 to 6 carbon atoms, or $R_1$ and $R_2$ together can form an alkylene chain having up to 6, preferably 4 to 5, carbon atoms, whereby the amines are selected so that the total number of carbon atoms give an amine which is liquid at the reaction conditions. Aliphatic amines are preferred. As examples of suitable amines can be mentioned triethylamine, diethylmethylamine, N-methyl pyrrolidine and N-methyl piperidine. The use of blends of two or more amines is, of course, also within the scope of the invention. Triethylamine (TEA) is the preferred tertiary amine, mainly for its physical properties and for economic reasons. The tertiary amine in the present process fulfils both the function of removing hydrogen halide from the fatty acid halide and the function of acting as a solvent/diluent for the respective reaction phases, preventing the reaction mixture from becoming too thick and viscous. The AKD produced during the reaction also contributes to the solvent/diluent effect as well as the unreacted amine. In order to fulfil the hydrogen halide removing function and the solvent/diluent functions the tertiary amine is suitably used in amounts of at least 1.15 moles and suitably an excess of tertiary amine is used so that the reaction is carried out with at least 1.5 moles, per mole of fatty acid halide. The upper limit is not critical but is set mainly for the obvious practical reason not to add the amine in amounts which do not contribute to the process and will just have to be removed. Usually the upper limit does not exceed 10 moles and most often it will not exceed 5 moles. Preferably tertiary amines in amounts of from 1.8 to 10 moles, and especially from 2 to 4, of amine per mole of fatty acid halide are used.

In the present process it is preferred that a major part of the excess of tertiary amine with regard to the fatty acid halide is removed in the stripping step. The proportion of the tertiary amine that can be removed by stripping will, of course, depend on the initial excess of amine and the equipment used. Suitably, at least 60% by weight of the molar excess of tertiary amine is removed by stripping before the acid extraction. This reduction of tertiary amine content in the reaction mixture gives productivity advantages in comparison with any process utilizing acid extraction as a single step to remove the excess of tertiary amine. Preferably at least 70% and most preferably at least 80% by weight of the molar excess of tertiary amine is removed by stripping before the acid extraction.

The following will illustrate suitable conditions for the process according to the invention for the production of AKD from hardened tallow fatty acid chloride and triethylamine. Suitable conditions for other fatty acid halides and other tertiary amines are easily determined by the man skilled in the art taking into consideration for example the melting points of the fatty acid halide and the produced AKD, respectively, and the physical properties of the tertiary amine. The process is suitably carried out by first charging the tertiary amine to a reactor and initially heating this to a temperature of at least 40° C. The temperature is dependent on the boiling point/melting point of the tertiary amine and acid halide respectively. In a process using TEA the initial heating is suitably carried out to a temperature of 40° to 60° C. The acid halide is then added, and suitably sub-surface in a continuous manner, to the heated tertiary amine phase and the addition time is suitably at least 0.5 hour. The addition is preferably carried out within a time period of from 1 to 4 hours, preferably within from 1 to 2 hours. The reaction between the fatty acid halide and the tertiary amine is exothermic and the reaction is thus usually carried out under cooling and the temperature during the reaction is suitably kept within the range of from 50° to 60° C., preferably within the range of from 50° to 55° C. The reaction is completed almost immediately when all the acid halide has been added. This is an indication that a continuous process can be operated if desired. The present process does not require a long post-reaction time and is thus also in this aspect advantageous in comparison with the conventional solvent-based processes since they usually require a post-reaction time of 2 to 2.5 hours. A further advantage is the fact of a smaller batch volume which leads to greater throughput and increased productivity.

After completed reaction the produced ketene dimer is separated from the formed crystals of tertiary amine hydrogen halide and the remaining tertiary amine. According to the present process the produced ketene dimer is obtained by stripping of the tertiary amine followed by separation of the formed crystals of tertiary amine hydrogen halide by acid extraction. Further remaining tertiary amine present in the reaction mixture after the stripping step can be removed in the acid extraction step by conversion to the corresponding amine salt. The stripping step is carried out under reduced pressure and suitably at a temperature of from 50° to 60° C., preferably 55° to 57° C. The acid extraction step is carried out by addition of inorganic acid, such as hydrochloric acid or sulphuric acid, suitably hydrochloric acid. Aqueous acid is preferably used. The extraction step is suitably carried out under stirring and at a temperature of from about 60° C. to about 80° C. The concentration of acid is dependent on the amount of amine remaining in the slurry. Calculations are based on an excess of acid at a concentration to produce a triethylamine salt solution of from 40 to 60% by weight water. The aqueous phase formed in the acid extraction step is separated from the AKD.

The AKD can be worked up in per se conventional manner and usually a water wash is carried out to remove impurities followed by a dehydration step to remove remaining water. The water wash is suitable carried out at a temperature of from 50° to 90° C. under stirring. A dehydration step usually involves heating to temperatures of from about 80° to about 90° C. under vacuum for about 30 minutes to about 1 hour. If desired, depending on the purity requirements in the intended use of the AKD, a filtration step can be carried out as a last step in order to remove any minor amounts of tertiary amine hydrogen halide and solid residues that may remain.

The AKD produced according to the present process is as pure as AKD produced according to conventional processes and in addition it is solvent-free and does not cause any problems when used as a sizing agent. In this field it can be used as conventionally in aqueous dispersions which can contain anionic, cationic or amphoteric dispersing agents. Usually AKD dispersions contain anionic dispersion agents, such as lignosulphonates or sodium salts of condensed aromatic sulphonic acids, and cationic polymers, for example cationic starch or cationic synthetic polymers such as polyacrylamide, polyamines etc.

The tertiary amine recovered in the stripping step as described above can of course be re-used directly. The aqueous phase obtained after the acid extraction step described above will have to be worked up in order for the tertiary amine to be re-used. Such a work-up will, as conventionally, involve neutralisation with alkali, suitably caustic soda, to liberate free amine from the hydrogen chloride salt. Any small amounts of water in the free amine are then suitably removed to bring the water content down to less than 1200 ppm, preferably less than 200 ppm before re-use. Dehydration of the amine can for example be carried out by fractional distillation, chemical treatment, e.g. with calcium hydride or molecular sieves, or a combination thereof.

The invention is further illustrated in the following examples which, however, are not intended to limit the same.

EXAMPLE 1

Comparison

In this example AKD was produced according to the toluene process.

111.5 g (1.1 moles) of triethylamine (water content less than 500 ppm) and 226.8 g (2.49 moles) of toluene were added to a clean, dry 1 liter jacketed vessel. The vessel was fitted with a stirring rod, thermometer, acid chloride inlet tube, nitrogen inlet and gaseous outlet via water cooled condenser. The vessel was purged with nitrogen and the contents heated to 50° C.

289.0 (1 mole) of tallow fatty acid chloride were pumped into the triethylamine/toluene mixture with stirring. The rate of acid chloride addition was adjusted to give an overall addition time of 1½ hour. During acid chloride addition the temperature was kept between 52° and 55° C. with nitrogen purge on both reaction vessel and acid chloride flask. After acid chloride addition had finished the reaction slurry was heated to 70° C. and stirred for 2 hours.

An acid extraction step was then carried out using 22.5 g of concentrated hydrochloric acid (36% w/w) added to 132.8 g of water and warmed to 60° C. The acid was added to the reaction slurry, stirred for 10 minutes and allowed to separate for 15 minutes. The lower triethylaminehydrochloride aqueous layer was drained off. A water wash was carried out by the addition of 100 mls of water, stirring for 30 second and allowing then to separate for 1½ hours at 70° C. Dehydration, filtration and evaporation of toluene was carried out. 256.5 g of AKD were obtained.

Assay by IR (content of 3-alkyl-4-alkylidenyl-oxetan-2-one) gave 88.5% w/w of AKD. GPC analysis gave: high molecular weight=8.6% medium (AKD) molecular weight=88.8% low molecular weight=2.6%

EXAMPLE 2

The reaction equipment were set up similar to Example 1 with additional distillation apparatus. A cold trap (−45° C.) was placed between triethylamine receiver and vacuum pump.

253.2 g (2.5 moles) of triethylamine were added to the vessel and heated to 50° C. 289.0 g (1 mole) of acid chloride, the same as in Example 1, were added in the same manner as in Example 1 holding temperature from 50° to 53° C. throughout addition. After acid chloride addition had finished vacuum was applied until the mixture began to boil at 57° C. Distillation was carried out for 1½ hours. An acid extraction was prepared by the addition of 62.2 g concentrated hydrochloric acid to 121.1 g of water and warming to 70° C. The acid was added to the reaction slurry and stirring was carried out for 10 minutes with separation for 15 minutes. The lower aqueous layer was drained off and the AKD layer was heated to 80° C. 100 mls of water were then added, stirred for 10 seconds and allowed to separate for 1 hour. The aqueous layer was drained off and then the product was dehydrated under reduced pressure followed by filtration as in Example 1. 254.4 g of AKD were obtained.

Assay by IR gave 87.9% w/w of AKD. GPC analysis gave: high molecular weight=9.6% medium (AKD) molecular weight=87.3% low molecular weight=3.1%

EXAMPLE 3

The same equipment as in Example 2 was used. 202.66 g (2 moles) of triethylamine were added to the vessel and heated to 47° C. 289.0 g (1 mole) of acid chloride, same as in Example 1, were added in 2 hours using cooling to hold the temperature from 53° to 56° C. during the addition. After acid chloride addition was finished the slurry was heated to 57° C. and stirred for 10 minutes before distillation, as in Example 2, for 40 minutes. Acid extraction was carried out using 52.7 g of concentrated hydrochloric acid to 148.8 g of water. Acid extraction and work up was carried out as in Example 2. 253.9 g of AKD were obtained.

Assay by IR gave 88.5% w/w of AKD. GPC analysis gave: high molecular weight=9.5% medium (AKD) molecular weight=88.5% low molecular weight=2.0%

EXAMPLE 4

The same reaction equipment as in Example 2 was used. 180.55 g (2.07 moles) of diethylmethylamine, water content less than 200 ppm, were added to the vessel and heated to 48° C. 237.0 g (0.82 moles) of acid chloride, same as in Example 1, were added in 100 minutes using cooling to hold the temperature from 52°–55° C. After acid chloride addition had finished, the reaction slurry was heated to 56° C. and stirred for 10 minutes before distillation of the amine for 40 minutes, as in Example 2. Acid extraction and work up was carried out in the same manner as in Example 2 using 40.89 g of concentrated hydrochloric acid with 107.11 g of water as acid extraction. 202.7 g of AKD were obtained.

Assay by IR gave 90.5% w/w of AKD. GPC analysis gave: high molecular weight=6.1% medium (AKD) molecular weight=92.9% low molecular weight=1.0%

I claim:

1. A process for the production of a ketene dimer from a fatty acid halide by reaction with a tertiary amine, comprising the steps of:
   (a) reacting a fatty acid halide and a tertiary amine in the substantial absence of inert solvent and in a molar ratio of tertiary amine to fatty acid halide of at least 1.15:1, thereby forming a reaction mixture comprising ketene dimer, tertiary amine hydrogen halide and unreacted tertiary amine;
   (b) stripping unreacted tertiary amine from the reaction mixture; and
   (c) separating crystals of tertiary amine hydrogen halide from the ketene dimer by acid extraction of the mixture at step (6).

2. A process according to claim 1, wherein not more than 5% by weight of additional solvent, based on the amount of fatty acid halides is present in the reaction mixture.

3. A process according to claim 1, wherein at least 1.5 moles of tertiary amine is used per mole of fatty acid halide.

4. A process according to claim 3, wherein from 1.8 to 10 moles of tertiary amine are used per mole of fatty acid halide.

5. A process according to claim 1, wherein the tertiary amine is $R_1R_2R_3N$, wherein $R_1$, $R_2$ and $R_3$ are the same or different and are selected from alkyl, alkenyl or cycloalkyl groups having from 1 to 6 carbon atoms, or $R_1$ and $R_2$ together forming an alkylene chain having up to 6 carbon atoms.

6. A process according to claim 5, wherein the tertiary amine is triethylamine, diethylmethylamine, N-methyl pyrrolidine or N-methyl piperidine.

7. A process according to claim 1, wherein the fatty acid halide is a chloride of a saturated or unsaturated fatty acid having from 12 to 22 carbon atoms.

8. A process according to claim 7, wherein the fatty acid halide is a chloride of a saturated or unsaturated fatty acid having from 16 to 18 carbon atoms.

9. A process according to claim 1, wherein said process is carried out in the complete absence of additional solvent.

10. A process according to claim 1, wherein at least 60% by weight of tertiary amine in step (6) is removed by stripping.

11. A process according to claim 1, wherein the stripping of the tertiary amine is carried out at reduced pressure.

12. A process according to claim 4, wherein from 2 to 4 moles of tertiary amine are used per mole of fatty acid halide.

13. A process according to claim 1, wherein the acid extraction is carried out by addition of inorganic acid.

14. A process according to claim 13, wherein the acid extraction is carried out using hydrochloric acid or sulfuric acid.

* * * * *

UNITED STATES PATENT AND TRADEMARK OFFICE
CERTIFICATE OF CORRECTION

PATENT NO.  : 5,399,774
DATED       : March 21, 1995
INVENTOR(S) : Paul S. McINTOSH It is certified that error appears in the above-indentified patent and that said Letters Patent is hereby corrected as shown below:

At Column 6, delete lines 18-19, and substitute therefor:

--   high molecular weight       = 8.6%
       medium (AKD) molecular weight = 88.8%
       low molecular weight        = 2.6%--.

At Column 6, delete lines 47-49, and substitute therefor:

--sis gave:

high molecular weight       = 9.6%
       medium (AKD) molecular weight = 87.3%
       low molecular weight        = 3.1%--.

At Column 6, delete lines 66-68, and substitute therefor:

--sis gave:

high molecular weight       = 9.5%
       medium (AKD) molecular weight = 88.5%
       low molecular weight        = 2.0%--.

At Column 7, delete lines 18-20, and substitute therefor:

--sis gave:

high molecular weight       = 6.1%
       medium (AKD) molecular weight = 92.9%
       low molecular weight        = 1.0%--.

UNITED STATES PATENT AND TRADEMARK OFFICE
CERTIFICATE OF CORRECTION

PATENT NO. : 5,399,774
DATED : March 21, 1995
INVENTOR(S) : Paul S. McINTOSH

It is certified that error appears in the above-indentified patent and that said Letters Patent is hereby corrected as shown below:

Column 7, claim 1, line 35, "of step (b)" should read --in step (b)--

Column 8, claim 10, line 26, "step (b)" should read --of step (b)--.

Signed and Sealed this

Twenty-third Day of January, 1996

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,399,774  
DATED : March 21, 1995  
INVENTOR(S) : Paul S. McINTOSH Page 1 of 2

It is certified that error appears in the above-indentified patent and that said Letters Patent is hereby corrected as shown below:

At Column 6, delete lines 18-19, and substitute therefor:

--     high molecular weight           = 8.6%  
      medium (AKD) molecular weight = 88.8%  
      low molecular weight           = 2.6% --.

At Column 6, delete lines 47-49, and substitute therefor:

--sis gave:

high molecular weight           = 9.6%  
      medium (AKD) molecular weight = 87.3%  
      low molecular weight           = 3.1% --.

At Column 6, delete lines 66-68, and substitute therefor:

--sis gave:

high molecular weight           = 9.5%  
      medium (AKD) molecular weight = 88.5%  
      low molecular weight           = 2.0% --.

At Column 7, delete lines 18-20, and substitute therefor:

--sis gave:

high molecular weight           = 6.1%  
      medium (AKD) molecular weight = 92.9%  
      low molecular weight           = 1.0% --.

UNITED STATES PATENT AND TRADEMARK OFFICE
CERTIFICATE OF CORRECTION

PATENT NO.  : 5,399,774
DATED       : March 21, 1995
INVENTOR(S) : Paul S. McINTOSH It is certified that error appears in the above-indentified patent and that said Letters Patent is hereby corrected as shown below:

Column 7, claim 1, line 35, "at step (6)" should read --of step (b)--.

Column 8, claim 10, line 26, "step (6)" should read --step (b)--.

This certificate supersedes Certificate of Correction issued January 23, 1996.

Signed and Sealed this

Twenty-eighth Day of May, 1996

Attest:

BRUCE LEHMAN

*Attesting Officer*    *Commissioner of Patents and Trademarks*